United States Patent [19]

Horrobin

[11] 4,302,447

[45] * Nov. 24, 1981

[54] PHARMACEUTICAL AND DIETARY COMPOSITION

[75] Inventor: David F. Horrobin, Montreal, Canada

[73] Assignee: Efamol Limited, London, England

[ * ] Notice: The portion of the term of this patent subsequent to Jun. 16, 1998, has been disclaimed.

[21] Appl. No.: 89,293

[22] Filed: Oct. 30, 1979

Related U.S. Application Data

[63] Continuation-in-part of Ser. No. 4,924, Jan. 19, 1979.

[30] Foreign Application Priority Data

| Jan. 23, 1978 | [GB] | United Kingdom | 2642/78 |
| Feb. 7, 1978 | [GB] | United Kingdom | 4921/78 |
| Apr. 19, 1978 | [GB] | United Kingdom | 15481/78 |
| Aug. 17, 1978 | [GB] | United Kingdom | 33682/78 |
| Oct. 24, 1978 | [GB] | United Kingdom | 41761/78 |

[51] Int. Cl.³ .............. A61K 33/30; A61K 31/54; A61K 31/43; A61K 31/20
[52] U.S. Cl. ............................ 424/145; 424/246; 424/271; 424/312; 424/318
[58] Field of Search .............. 424/145, 246, 271, 312, 424/318

[56] References Cited

U.S. PATENT DOCUMENTS

| 1,926,745 | 9/1933 | Klopfer | 424/145 |
| 3,923,982 | 12/1975 | Lamand et al. | 424/145 |
| 4,034,099 | 7/1977 | Bryan | 424/271 |
| 4,058,594 | 11/1977 | Williams | 424/312 |

FOREIGN PATENT DOCUMENTS

| 2272684 | 1/1975 | France | 424/271 |
| 7500325 | 12/1975 | France | 424/312 |
| 1391449 | 4/1975 | United Kingdom | 424/271 |

OTHER PUBLICATIONS

U. K. Publication, *Here's Health*, p. 10, 1977.
*Lancet*, Apr. 30, 1977, p. 936.
*Chem. Abstr.*, vol. 77, 1972, 39210h; 83 (1975) 15501b; 83 26534r (1975).

*Primary Examiner*—Frederick E. Waddell
*Attorney, Agent, or Firm*—Cushman, Darby & Cushman

[57] ABSTRACT

Compositions and use of γ-linolenic acids and related materials alone or with zinc and or β-lactam antibiotics to treat schizophrenia, obesity, menstrual disorders, skin disorders and other conditions, and β-lactam antibiotics alone to treat schizophrenia.

14 Claims, No Drawings

PHARMACEUTICAL AND DIETARY COMPOSITION

This application is a continuation-in-part of U.S. application Ser. No. 4,924, filed Jan. 19, 1979.

FIELD OF THE INVENTION

This invention relates to the treatment of various diseases and disorders primarily, but not exclusively, in the field of human medicine and to pharmaceutical and dietary compositions for use therein.

GENERAL BACKGROUND

Considerable interest has been shown in recent years in the use of prostaglandin (PG) precursors in medicine.

For various reasons it is not practical to administer naturally-occurring prostaglandins such as PGE 1 and PGE 2 to patients. Consequently, considerable attention has focussed on the use of prostaglandin precursors including linoleic acid (9,12octadecadienoic acid), γ-linolenic acid (6, 9, 12-octadecatrienoic acid) and dihomo-γ-linolenic acid (5, 8, 11-eicosatrienoic acid), conversion in the body being believed to be as follows:

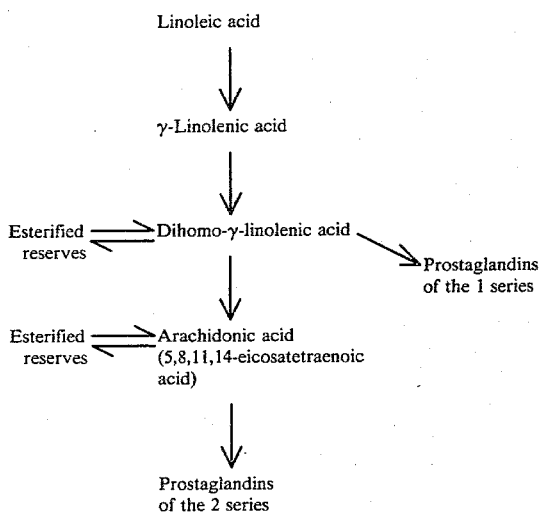

DESCRIPTION OF THE PRIOR ART

Prior art within this general area includes the following patents and papers.

(i) U.S. Pat. Nos. 3,993,775 (issued Nov. 23, 1976) and 4,058,594 (issued Nov. 15, 1977) of John Williams, which describe a method of providing an immuno-suppressive effect in a patient undergoing organ or tissue transplant or suffering from multiple sclerosis comprising administration of a daily dosage of from 5 mg to 3 g of γ-linolenic acid or dihomo-γ-linolenic acid or a functional derivative thereof.

(ii) British Patent Specification No. 1 082 624, published Sept. 6, 1967, (Calmic Limited), which discloses effectiveness of γ-linolenic acid in the treatment of vascular diseases.

(iii) McCormack, Neil and Sim (The Lancet, page 308, Sept. 3, 1977), who describe preliminary work on the use of an oil containing a mixture of linoleic and γ-linolenic acid (as triglycerides) in in the treatment of rheumatoid arthritis.

(iv) Sim and McCraw (Thrombosis Research Volume 10, pages 385-397, 1977), who describe activity of the methyl esters of γ-linolenic acid and dihomo-γ-linolenic acid in vitro and in vivo on blood platelet function in non-human primates and in man.

(v) French Patent Specification No. 2 272 684 (Ito), which discloses enhancement of antibiotic action by sundry unsaturated fatty acids including [α] linolenic acid.

The present inventor has discovered a number of new applications of γ-linolenic acid and dihomo-γ-linolenic acid in therapy, alone and in conjunction with zinc, β-lactam antibiotics or other materials influencing the 1-series/2-series PG balance in the body in favour of 1-series PG's, herein referred to as 1-series PG enhancers and fully discussed later. These applications are now described in turn, with one particular use of the antibiotics alone.

SCHIZOPHRENIA

In the Lancet, page 936, April 30, 1977 the present inventor has suggested that schizophrenia is a prostaglandin deficiency disease. Schizophrenia is not a disorder which would suggest the use of immuno-suppressive drugs. The specific suggestion was made that arachidonic acid, known to a precursor of prostaglandins of the 2-series should alleviate schizophrenia.

As a result of further research, the present inventor now believes that schizophrenia is due not to a deficiency of 2-series PG's but rather to a deficiency of PGE 1 and other PG's of the 1-series, of which arachidonic acid is not a precursor, or an imbalance in the normal ratio of 1-series and 2-series PG's.

This has led to the realisation that the precursor(s) which should be used to stimulate the natural production of 1-series PG's in the treatment of schizophrenia should include γ-linolenic acid and/or dihomo-γ-linolenic acid, either or both of which may be used in association with linoleic acid and if desired other fat acids. Although these substances are 2-series PG precursors (via arachidonic acid) as well as 1-series PG precursors, this is not deleterious to their use, although one may require to use relatively higher amounts of precursors than would be the case if only 1-series PG's were being biosynthesized.

Accordingly, in one aspect of the invention, there is provided a method of treating schizophrenia in a patient which comprises administering to the patient an effective amount of γ-linolenic acid and/or dihomo-γ-linolenic acid, optionally in association with linoleic acid and if desired other fat acids, said acids being used, if desired, as physiologically functional derivatives thereof.

From another aspect the invention provides a pharmaceutical or dietary composition for the treatment of schizophrenia comprising γ-linolenic acid or physiologically functional derivative thereof and/or dihomo-γ-linolenic acid or physiologically functional derivative thereof, alone or in an acceptable pharmaceutical or dietary vehicle.

A preferred daily dosage for an adult (weight ca 75 kg) is from 0.05 or 0.1 up to 1, 2, 5 or even 10 g as required of γ-linolenic acid or equivalent weight (calculated as γ-linolenic acid) of physiologically functional derivative thereof. Amounts may in particular be 0.1 to 1.0 g daily. In place of, or in addition to, γ-linolenic acid, one may use dihomo-γ-linolenic acid or a physiologically functional derivative thereof, in amounts equivalent in molar terms to γ-linolenic acid and calculated as such. This dosage can for example be taken as a single dose or divided into 2, 3 or 4 subdivisions thereof as convenient.

The present inventor has further surprisingly found that β-lactam antibiotics, for example phenoxymethyl penicillin (penicillin V), are able to stimulate the production of PG's of the 1-series in rats, and moreover that the use of such compounds in the treatment of patients suffering from "classic" schizophrenia has indicated that they have an antipsychotic activity.

Thus according to a further aspect, the invention provides a method of treating schizophrenia in a patient which comprises administering an effective amount of a β-lactam antibiotic.

From another aspect, the invention provides pharmaceutical compositions comprising a β-lactam antibiotic for use in the treatment of schizophrenia.

β-lactam antibiotics which may be used according to the present invention, are conveniently any of the known penicillin and cephalosporin antibiotics (including semi-synthetic antibiotics) such as, for example, penicillin G, penicillin N, penicillin V, cephalexin, cephalothin, ampicillin, amoxycillin, cloxacillin and cephaloglycin. Any of these may be used in the form of their physiologically functional non-toxic derivatives, for example alkali metal salts e.g. sodium and potassium salts, and salts with organic bases, and reference to an antibiotic herein (including the claims) includes reference to such derivatives.

The antibiotics may for example be administered orally, parenterally or rectally as desired.

The antibiotic is preferably administered in the form of dosage units. Suitable daily dosages of said active ingredient may for example be in the range 0.5 to 3.0 g per day in patients of average weight. Such daily dosages may conveniently be divided into for example, two, three or four equal doses to be administered two, three or four times daily respectively.

In severely disturbed patients it may be desirable to additionally administer conventional tranquillizers in addition to regular treatment with penicillin, but this is only required when such patients experience extreme agitation, insomnia or hallucinations.

The use of penicillins in the long term treatment of schizophrenia is especially desirable in view of the known relative absence of side effects of these drugs. Thus, penicillin has been administered for many years to patients having rheumatic heart disease in order to prevent streptococcal infections, and there is virtually no evidence of long term toxicity.

Care should of course be taken to ensure that the patient is not allergic to the drug of choice. With respect to the known ability of penicillins to produce reactions in some patients due to penicillin hypersensitivity, there is evidence to suggest that schizophrenics have a reduced incidence of allergic reactions and more particularly of penicillin hypersensitivity. Thus, the problem, usually associated with penicillin antibiotic therapy, of hypersensitization in a small number of patients, is not quite so important in the treatment of schizophrenia using penicllins.

A valuable benefit of the present invention is that the hitherto extensively used chemotherapeutic agents for schizophrenia have been associated with a tranquillizing activity, with the result that the use of these drugs in therapy is combined with an often undesired heavy sedation of the patient. Also such drugs may be responsible for the production of irreversible damage in up to 70% of patients to those parts of the brain which control movement. Avoidance or substantial avoidance of the use of these drugs is thus of great value.

It is of particular value to combine the above two new approaches and accordingly, in a further aspect of the invention, there is provided a method of treating schizophrenia in a patient which comprises administering to the patient an effective amount of a 1-series PG enhancer, in particular, a β-lactam antibiotic or (as described later herein) zinc, together with γ-linolenic acid and/or dihomo-γ-linolenic acid, said acids being used, if desired, as physiologically functional derivatives thereof, and if desired in association with linoleic acid or other fat acids.

β-lactam antibiotics which may be used are conveniently as above.

The dosages also are suitably as above, in conjunction with the amounts of γ-linolenic acid, dihomo-γ-linolenic acid or equivalent derivative specified, in particular 0.1 to 1.0 g daily.

The invention further provides the pharmaceutical compositions for the treatment of schizophrenia comprising a β-lactam antibiotic, zinc or other 1-series PG enhancer in association with γ-linolenic acid and/or dihomo-γ-linolenic acid together if desired with linoleic acid and/or other fat acids, the active acids being used, if desired, as physiologically functional derivatives thereof.

Alternatively, if it is not desired to have compositions comprising both the 1-series PG enhancer and the γ-linolenic or other acid or derivatives, packs may be prepared comprising the active materials presented for separate administration in the appropriate relative amounts, and such packs are within the purview of the invention.

SKIN DISORDERS

A further area where the administration of 1-series PG precursors is indicated is in the treatment of psoriasis and other human skin disorders such as acne, dandruff, eczema and hair loss (other than that due to inherited male pattern baldness).

According to the invention therefore, there is provided a method of treating the above conditions in a patient which comprises administering an effective amount of γ-linolenic acid and/or dihomo-γ-linolenic acid, or physiologically functional derivatives thereof, as set out above in relation to schizophrenia, both as to preferred amounts and as to optional association with other acids.

There is also provided a pharmaceutical or dietary composition for the treatment of such disorders comprising γ-linolenic acid or physiologically functional derivative thereof and/or dihomo-γ-linolenic acid or physiologically functional derivative thereof, alone or in an acceptable pharmaceutical or dietary vehicle.

The physiological basis for these treatment is not understood in detail but it is believed by the present inventor that conditions such as psoriasis, dandruff, eczema and hair loss are related to each other by common, or at least related, defects in 1-series PG precursor metabolism, expressing themselves in various ways in different individuals. Experimental evidence of a relation is discussed below in the section on veterinary application of the invention.

OBESITY

A current technique for the treatment of obesity involves the administration of linoleic acid, generally in the form of vegetable oils such as sunflower oil and/or corn oil. In order to be effective, these current dietary approaches to the treatment of obesity require the intake of other fats in the diet to be substantially reduced. In the body, linoleic acid is converted as described earlier and the present inventor believes that the beneficial effect of administration of linoleic acid is due to enhancement of 1-series PG production and in particular of PGE 1, this substance causing a metabolic shift increasing appetite and reducing weight. However, the presence of other fats in the diet interferes with the conversion of linoleic acid to γ-linolenic acid and thus reduces the effectiveness of the treatment.

What is not proposed is administration of γ-linolenic acid and/or dihomo-γ-linolenic acid as effective in the treatment of obesity, even when other fats are present in the diet.

According to the invention, therefore, there is provided a method of treating obesity in a patient which comprises administering to the patient an effective amount of γ-linolenic and/or of dihomo-γ-linolenic acid or physiologically functional derivatives thereof as set out above in relation to schizophrenia both as to preferred amounts and as to optional association with other acids. Amounts may in particular be for example 0.5 to 10 g of γ-linolenic acid or equivalent daily.

The invention further provides a pharmaceutical or dietary composition for the treatment of obesity comprising γ-linolenic acid or physiologically functional derivative thereof and/or dihomo-γ-linolenic acid or functional derivative thereof, alone or in an acceptable pharmaceutical or dietary vehicle.

MENSTRUAL DISORDERS

Menstrual disorders are not uncommon and while they do not usually require clinical treatment they are often a cause of distress or discomfort. Such disorders include: extended periods of blood loss, sometimes for as long as 9 days or more, especially when using intra-uterine contraceptive devices; excessive blood loss during menstrus, which is again often associated with the use of intra-uterine contraceptive devices; so-called "period pains"; premenstrual swelling associated with excessive fluid retention; and irregular menstrual cycle lengths.

The present inventor has now surprisingly found that the administration of γ-linolenic acid and/or dihomo-α-linolenic acid optionally together with linoleic acid causes a significant reduction in some or all of the above mentioned menstrual disorders.

Accordingly, the invention provides a method of treating menstrual disorders which comprises administering an effective amount of γ-linolenic acid and/or dihomo-γ-linolenic acid or physiologically functional derivatives thereof, as set out above in relation to schizophrenia both as to preferred amounts and as to optional association with other acids. Amounts may in particular be for example 0.1 to 0.5 g of γ-linolenic acid or equivalent daily.

The invention further provides a pharmaceutical or dietary composition for the treatment of menstrual disorders comprising γ-linolenic acid or physiologically functional derivative thereof and/or dihomo-γ-linolenic acid or functional derivative thereof, alone or in an acceptable pharmaceutical or dietary vehicle.

In tests which have been effected by the present inventor, it has been found that women previously exhibiting excessive periods of blood loss during menstrus experienced a reduction in this period to 3 to 5 days on treatment according to the invention. In addition these tests have shown that a reduction in amount of blood loss, period pains and premenstrual swelling and a stabilisation of menstrual cycle lengths, may be achieved when treating women according to the invention.

The physiological explanation for the efficacy of the treatment according to the invention is not fully understood. However, whilst not wishing to be bound by theoretical considerations, the inventor has noted that these types of menstrual disorders are often associated with obesity, which appears in at least some subjects to be due to a deficiency in essential fatty acids.

DIETARY COMPOSITIONS

The invention is chiefly described in terms of pharmaceutical compositions, but it will be understood that the γ-linolenic and other acids, being in the nature of dietary supplements, could if available at an economic price be incorporated in a dietary margarine or other foodstuff; such foodstuffs, referred to herein as dietary compositions, are within the purview of the invention.

VETERINARY APPLICATIONS

It will be understood that where a disorder of a kind calling for treatment in animals arises, the invention while described primarily in terms of human medicine and treatment is equally applicable in the veterinary field.

Thus for example domestic cats have an unusual dietary requirement in essential fatty acids, being apparently unable to convert linoleic acid to γ-linolenic acid and dihomo-γ-linolenic acid to arachidonic acid. They are liable to a group of related skin conditions with hair loss, dandruff, scaling, pruritis, easy breakdown of the skin with rubbing or scratching, and defective healing, all of which can also be produced experimentally by an EFA (essential fatty acid) deficient diet, evidencing their related nature. Similar conditions can be produced experimentally in other animals, with skin lesions similar to eczema and psoriasis. Feeding of γ- or dihomo-γ-linolenic acid is effective in reversing the conditions, including, perhaps surprisingly, those in cats. This indicates, in view of the arachidonic acid block, that the conditions are indeed, as the present inventor believes also for the human skin conditions discussed above, related to 1 series PG deficiencies. The spontaneous conditions observed in cats are for example relieved by giving 0.5 g of Oenothera oil per day, five days a week.

FORMS AND SOURCES OF γ-LINOLENIC AND OTHER ACIDS

Convenient physiologically functional derivatives of γ-linolenic acid and dihomo-γ-linolenic acid for use according to the invention for all the purposes described include the $C_1$–$C_4$ alkyl (e.g. methyl and ethyl) esters and the glycerides of the acids.

If desired, pharmaceutical compositions may be produced for use in the invention by associating natural or synthetic γ-linolenic acid (or a physiologically functional derivative thereof) and/or dihomo-γ-linolenic acid (or a physiologically functional derivative thereof)

as such, with an acceptable pharmaceutical vehicle. It will however generally be convenient to incorporate the γ-linolenic acid into compositions in the form of an available oil having a high γ-linolenic acid content.

At the present time known natural sources of oils having a high γ-linolenic acid content are few (there are no known natural sources of significant amounts of dihomo-γ-linolenic acid). One source of oils currently available is the seed of Evening Primrose species such as *Oenothera biennis L.* and *Oenothera lamarckiana*, the oil extract therefrom containing γ-linolenic acid and linoleic acid in the form of their glycerides together with other glycerides. Another source of γ-linolenic acid is the seed of Borage species such as *Borago officinalis* which, though its current yield per acre is low, provides a richer source of γ-linolenic acid than Oenothera oil. Recent studies on fungi which can be cultivated by fermentation promise a fungal oil source.

The seed oil extracts referred to above can be used as such or can if desired be fractionated to yield an oily composition containing the triglycerides of γ-linolenic acid and linoleic acid as the only fatty acid components, the γ-linolenic acid content being a major proportion. Seed oil extracts appear to have a stabilising effect upon any dihomo-γ-linolenic acid or physiologically functional derivative thereof incorporated therein.

USE OF 1-SERIES PG ENHANCERS GENERALLY AND ZINC IN PARTICULAR

As has been mentioned above, γ-linolenic acid and dihomo-γ-lenolenic acid function as precursors for both 1- and 2-series PG's. The pesent inventor believes it advantageous if the biosynthesis of 1-series PG's can be effected preferentially to that of 2-series PG's in conditions, not merely schizophrenia and the other new applications discussed herein in which 1-series PG imbalances or lack need to be corrected.

It has previously been believed that selective enhancement of 1-series PG formation and inhibition of 2-series PG formation are impossible because the mobilisation of DGLA reserves and the mobilisation of AA reserves have been thought to be the same reaction, mediated by the same phospholipase. Similarly the formation of 1-series endoperoxides from DGLA, leading to 1-series PG's has been thought inseparable from the formation of 2-series endoperoxides from AA, leading to 2-series PG's. The inventor however has evidence that these assumptions are not true and that agents may be found which regulate the reactions selectively; for example penicillin and zinc appear to activate DGLA mobilisation without effecting AA mobilisation and the formation of 1-series PG's is increased preferentially.

Most broadly, agents effective according to the invention are those which:

(a) selectively activate DGLA mobilisation or convention to endoperoxides, with small or no effect on AA mobilisation or conversion;

(b) inhibit conversion of DGLA to AA. (The body can make up any lack of AA from reserves to maintain 2-series PG production if required);

(c) selectively inhibit AA mobilisation or conversion to endoperoxides, with small or no effect on DGLA mobilisation or conversion. The materials referred to earlier herein as '1-series PG enhancers' that is to say materials influencing the 1-series/2-series PG balance in the body in favour of 1-series PG's, are thus believed to act by one or more of the above mechanisms.

Without restriction to the theory, the present inventor believes that zinc is an example of materials that tend to stimulate the biosynthesis of 1-series PG's and specifically that it potentiates mobilisation of esterified reserves of dihomo-γ-linolenic acid. This enables one to use zinc conjointly with γ-linolenic acid and/or dihomo-γ-linolenic acid.

The present invention thus further provides a method of treating a patient requiring 1-series PG therapy, which comprises administering to said patient an effective conjoint amount of zinc, or other 1-series PG enhancer and γ-linolenic acid and/or dihomo-γ-linolenic acid, or physiologically functional derivatives thereof, if desired in association with linoleic acid or other acids as discussed earlier. The presence of arachiodonic acid or any other material tending to oppose the PG 1 enhancing effect is to be avoided.

In particular, zinc or other 1-series PG enhancer may be given additionally in any of the specific methods of treatment using γ-linolenic acid, dihomo-γ-linolenic acid, or derivatives thereof described earlier. It may further be expected to be effective in the methods of treatment described in the prior patents and other publications referred to.

The invention also provides a pharmaceutical or dietary composition comprising (a) γ-linolenic acid or physiologically functional derivative thereof and/or dihomo-γ-linolenic acid or physiologically functional derivative thereof and (b) a conjoint amount of physiologically assimilable zinc or other 1-series PG enhancer, alone or in an acceptable pharmaceutical or dietary vehicle.

Based on present evidence, a suitable daily dosage of zinc for an adult (weight ca 75 kg) is 2.5–800 mg preferably 10–200 mg and advantageously 10–80 mg zinc daily, with γ-linolenic acid or other acid or equivalent in the amounts previously discussed. The 10–80 mg zinc is approximately 0.125–1.0 mg/kg adult body weight. In view of the conjoint effect of the zinc preferred amounts of γ-linolenic or other acid or equivalent are less than when zinc is not present, advantageously 0.1 to 1.0 g daily. As before the dosage can be taken as a single dose or divided into 2, 3 or 4 subdivisions thereof.

Conveniently the zinc or other 1-series PG enhancer and the γ-linolenic or other acid or derivatives are given together in a single preparation but they can of course be taken separately. The invention then provides not only the above compositions but also packs comprising the zinc or other material(s) and the γ-linolenic or other acid or derivative presented for separate administration in the appropriate relative amounts.

Zinc should be administered in a form in which it is readily taken up in vivo. Ordinarily this will indicate the use of a zinc salt of a mineral or organic acid, said salt being physiologically acceptable at the given dosage. Some zinc salts which would be contraindicated at higher dosages may be satisfactory for present purposes at the dosages indicated above. Useful salts include zinc sulphate and zinc gluconate and in particular zinc oleate, γ-linolenate and dihomo-γ-linolenate, and zinc oxide may also be employed. It is also possible to administer the zinc in chelated form. In any event, the preferred amounts of zinc are as stated above (the quantities given being calculated as zinc metal).

USE OF β-LACTAM ANTIBIOTICS

The use of γ-linolenic or other acids and derivatives, with β-lactam antibiotics, is discussed above in relation to schizophrenia. The present inventor believes that the reason for the effectiveness of the antibiotics is that, as he believes with zinc, they enhance utilisation of ester reserves of dihomo-γ-linolenic acid. Whether or not this is so, and no restriction to the theory is intended, zinc and antibiotics do appear to have parallel effects in treating all the conditions discussed herein when used with the γ-linolenic or other acids and derivatives. The compositions may further be expected to be effective in the methods of treatment described in the prior patents and other publications referred to.

It is also, further possible and has been found valuable to use both zinc and β-lactam antibiotic conjointly with the γ-linolenic acid, dihomo-γ-linolenic acid or derivatives as described earlier.

In all cases the amounts of active materials are as discussed already and association of the γ-linolenic or other acid with linoleic or other fat acids is possible.

Methods of treatment, pharmaceutical compositions and packs, as above, with the addition of an effective conjoint amount of β-lactam antibiotic, particularly penicillin V, with or without zinc are thus all within the invention, and the β-lactam antibiotics may of course be used with additional 1-series PG enhancers other than zinc.

PHARMACEUTICAL PRESENTATION

The compositions according to the invention are conveniently in a form suitable for oral, rectal, parenteral or topical administration in a suitable pharmaceutical vehicle, as discussed in detail for example in U.K. Patent Specification No. 1,082,624 and in any case known generally according to the type of preparation. Thus for example tablets, capsules, ingestible liquid or powder preparations, creams and lotions for topical application, or suppositories, can be prepared as required.

Advantageously a preservative such as α-tocopherol is incorporated into the preparations. α-Tocopherol in a concentration of about 0.1% by weight has been found suitable for the purpose.

It will be understood that the absolute quantity of active ingredients present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The following Examples serve to illustrate pharmaceutical compositions according to the invention:

EXAMPLES

Pharmaceutical compositions containing a unit dose of an oil extract from the seeds of *Oenothera biennis L.* optionally with methyl dihomo-γ-linolenate and/or zinc sulphate and/or penicillin V are prepared by encapsulation of the natural oil in soft gelatin capsules manufactured by known methods.

The oil is extracted from the seeds by one of the conventional methods of extraction such as cold pressure, screw pressure after partially cooking the seed, or solvent extraction.

Fractionation of a typical sample of this oil shows a yield of 97.0% oil in the form of methyl esters, with the relative proportions:

| | |
|---|---|
| Palmitate | 6.15 |
| Stearate | 1.6 |
| Oleate | 10.15 |
| Linoleate | 72.6 |
| γ-Linolenate | 8.9 |

As preservative, α-tocopherol is added to the oil in a concentration of 0.1%.

Gelatin capsules containing oil extracts prepared as described above, each having the following contents of active ingredients (0.5 g oil extract = ca 0.045 g γ-linolenic acid), are prepared in conventional fashion. The zinc may conveniently be incorporated as zinc oleate made by the method disclosed in Monatschrift 42 287 (1921) and similar methods may be applied to make for example zinc γ-linolenate if desired.

EXAMPLES, SCHIZOPHRENIA

Example 1

| | |
|---|---|
| Oil extract | 0.5 g |
| Zinc sulphate | 10 mg |

Two capsules may be administered thrice daily in the treatment of schizophrenia, giving a daily dose of γ-linolenic acid of ca 0.27 g. Capsules without zinc are an alternative.

Example 2

| | |
|---|---|
| Oil extract | 0.5 g |
| Methyl dihomo-γ-linolenate | 10 mg |
| Zinc sulphate | 10 mg |

Two capsules may be administered thrice daily in the treatment of schizophrenia, capsules without zinc being an alternative.

Example 3

| | |
|---|---|
| Oil extract | 0.5 g |
| Penicillin V | 0.25 g |

Two capsules may be administered thrice daily in the treatment of schizophrenia.

Example 4

| | |
|---|---|
| Oil extract | 0.5 g |
| Penicillin V | 0.25 g |
| Zinc sulphate | 10 mg |

Two capsules may be administered thrice daily in the treatment of schizophrenia.

Example 5

| | |
|---|---|
| Oil extract | 0.5 g |
| Methyl dihomo-γ-linolenate | 10 mg |
| Penicillin V | 0.25 g |
| Zinc sulphate | 10 mg |

Two capsules may be administered thrice daily in the treatment of schizophrenia.

Example 6

Penicillin V tablets 250 mg made by conventional methods may be administered in the treatment of schizophrenia, one tablet four times a day.

EXAMPLES, SKIN DISORDERS

Example 7

| | |
|---|---|
| Oil extract | 0.5 g |

Two capsules may be administered thrice daily in the treatment of acne.

Example 8

| | |
|---|---|
| Oil extract | 0.5 g |
| Zinc sulphate | 20 mg |

Two capsules may be administered thrice daily in the treatment of acne.

Example 9

| | |
|---|---|
| Oil extract | 0.5 g |

Two capsules may be administered thrice daily in the treatment of psoriasis.

Example 10

| | |
|---|---|
| Oil extract | 0.5 g |
| Zinc sulphate | 20 mg |

Two capsules may be administered thrice daily in the treatment of psoriasis.

Example 11

| | |
|---|---|
| Oil extract | 0.5 g |

Two capsules may be administered thrice daily in the treatment of eczema.

Example 12

| | |
|---|---|
| Oil extract | 0.5 g |
| Zinc sulphate | 20 mg |

Two capsules may be administered thrice daily in the treatment of eczema.

Example 13

| | |
|---|---|
| Oil extract | 0.5 g |

Two capsules may be administered thrice daily in the treatment of dandruff and loss of hair.

Example 14

| | |
|---|---|
| Oil extract | 0.5 g |
| Zinc sulphate | 20 mg |

Two capsules may be administered thrice daily in the treatment of dandruff and loss of hair.

EXAMPLES, OBESITY

Example 15

| | |
|---|---|
| Oil extract | 0.5 g |

Two capsules may be administered thrice daily in the treatment of obesity.

Example 16

| | |
|---|---|
| Oil extract | 0.5 g |
| Zinc sulphate | 20 mg |

Two capsules may be administered thrice daily in the treatment of obesity.

EXAMPLES, MENSTRUAL DISORDERS

Example 17

| | |
|---|---|
| Oil extract | 0.5 g |

Two capsules may be administered twice daily in the treatment of menstrual disorders.

Example 18

| | |
|---|---|
| Oil extract | 0.5 g |
| Methyl dihomo-$\beta$-linolenate | 10 mg |

Two capsules may be administered twice daily in the treatment of menstrual disorders.

Example 19

| | |
|---|---|
| Oil extract | 0.5 g |
| Zinc sulphate | 10 mg |

Two capsules may be administered twice daily in the treatment of menstrual disorders.

EVIDENCE OF EFFICACY

The conditions are considered in turn.

SCHIZOPHRENIA

1. Penicillin alone

A group of ten severe chronic schizophrenics stabilised on standard phenothiazine drug therapy and known to relapse without it were taken off these drugs and given penicillin V 300 mg four times a day, rising to 600 mg. In nine out of ten cases the stabilised condition was successfully maintained on the penicillin alone over many weeks, with benefit to the patients from the absence of the known phenothiazine side effects including sleepiness. One patient reacted adversely to the higher doses of penicillin and was returned to the previous therapy.

Further, a female patient aged 50 who had suffered for 20 years from severe schizophrenia and was aggressive, paranoid and hypochondriacal in spite of conventional drug treatment with haloperidol (10 mg tds) plus flupenthixol decanoate (40 mg/month), was taken off these drugs. After three weeks she was given penicillin V 250 mg qds. In the first week her symptoms became less severe and a steady improvement was maintained over five months.

2. Oenothera oil alone

Three further patients stabilised on standard phenothiazine drug therapy were taken off these drugs and instead given Oenothera oil, 2×0.6 ml capsules qds. The stabilised condition of each patient was maintained for several weeks.

3. Oenothera oil and penicillin together

The female patient referred to above was taken off the penicillin and after three weeks had again become markedly aggressive, paranoid and hypochondriacal. She was then given Oenothera oil (2×0.6 ml capsules qds) and penicillin V (250 mg qds). There was some initial nausea and headache but after two weeks hypochondriacal delusions ceased and after six weeks paranoid delusions, aggressiveness and incongruity of affect had also disappeared. Further, 6 kg in weight were lost in the course of 16 weeks in spite of a regular diet.

A further, male patient of 31 had suffered from severe schizophrenic illness for 12 years and had been an inpatient for 7 years, aggressive, hearing voices, of wild staring appearance and not speaking spontaneously to others. He had been receiving fluphenazine decanoate 75 mg every two weeks, benzhexol 5 mg three times a day and supplementary chlorpromazine as required. He was taken off these drugs and given Oenothera oil and penicillin as above for one month and an increase to 3 capsules qds in the oil thereafter. Over a period of six months he became co-operative, not easily upset by fellow patients, without aggressions, speaking spontaneously and appropriately to others, and with almost normal affect. His BPRS score dropped from 44 to 21 over the period.

Four other severe chronic schizophrenics controlled by phenothiazines were withdrawn from them and given the Oenothera oil and penicillin. The condition of each was maintained without the side effects of the other drugs.

4. Oenothera oil, pencillin and zinc

Preliminary trials with a small group of similar patients to those in the previous trials have been promising on the following:

Oenothera oil 6 or 8×0.6 ml capsules/day
Penicillin 250 mg qds
Zinc, as sulphate 20 to 40 mg/day

SKIN DISORDERS

Acne and psoriasis are two common and intractable conditions that have shown favourable results with treatment according to the invention.

Two groups of sufferers from severe acne, of 8 and 7 young men respectively, received Oenothera oil 0.6 ml and Oenothera oil 0.6 ml+zinc sulphate 20 mg, 6 capsules daily. All showed improvement in terms of reduction both in the number of inflamed facial pustules and in sebum production rate, over a period of 4 to 6 weeks, the group with zinc showing a greater improvement than the group without.

After three months all the subjects showed a very substantial improvement, most being essentially clear of pustules.

A group of 4 subjects with psoriasis was given similar treatment. In all, scaliness and itching were reduced, a group of three without zinc initially showing less improvement than a like group with, but catching up when changed to the capsules with zinc. In no case was there a full cure, but psoriasis is a particularly intractable condition in which even a modest improvement is clinically significant.

No clinical trials have been done on hair loss, but in a group of 30 laboratory rats maintained on a zinc deficient diet, hair loss was reversed by feeding of Oenothera oil with an increased effect when zinc was fed as well.

Preliminary results with eczema using Oenothera oil and zinc together have given favourable indications, as found with psoriasis. Dandruff also responded favourably in two individuals otherwise wholly healthy.

OBESITY

Thirty-eight healthy subjects took Oenothera oil in 0.6 ml capsules for 6–8 weeks, thirty-four of them at 6 capsules a day and four at eight capsules a day, while continuing to eat their normal diets.

Twenty-two of the subjects, all taking 6 capsules a day, were initially within 10% of their ideal body weight according to the standard life tables. None gained or lost more than 2 kg.

The other sixteen subjects were all more than 10% above their ideal body weight. Of this group, two women and three men showed no change in weight. they were taking 6 capsules a day. Six women and five men lost weight, as follows:

| | |
|---|---|
| Initial mean weight kg | 74.55 ± 7.94 (S.D.) |
| Final mean weight kg | 70.42 ± 6.52 |
| | (p ± 0.5, paired t test) |

Of the subjects who lost weight, four who were taking 8 capsules a day lost 8.2, 10.0, 10.9 and 12.7 kg respectively. All the other subjects who lost weight were taking 4 or 6 capsules a day.

These results indicate that overweight individuals, but not those of normal weight, have a good chance of losing weight by simple inclusion of Oenothera oil in the diet, and that the weight loss is dose related.

No adverse effects were observed. The intake of 6 capsules a day, 3.6 ml of the oil, is equivalent to ca 0.27 g of γ-linolenic acid; of 8 capsules a day, 4.8 ml of the oil, ca 0.36 g of γ-linolenic acid.

Preliminary results with a further group of subjects indicate improvement in terms of weight loss and proportion of subjects responding, when capsules containing 20 mg zinc sulphate in addition to the oil are used.

MENSTRUAL DISORDERS

A group of 15 women of reproductive age was treated, four of whom were using an intrauterine contraceptive device and all of whom were suffering from prolonged menstrus of 8 to 12 days with excess blood loss. Of these women, 5 also suffered from the premenstrual syndrome of depression, pain and fluid retention.

Administration of Oenothera oil 6×0.6 ml capsules daily over a period of several months consistently reduced the duration of blood loss to 3 to 5 days with concomitant reduction in the amount. The symptoms of the premenstrual syndrome in those women showing it became mild, or in one instance disappeared entirely and stayed gone for 3 full cycles, up to the end of the trial.

Preliminary results indicate a further improved affect of oil capsules containing also 20 mg zinc sulphate.

USE OF ZINC

Substantial clinical results are not at present available on all the conditions for which the use of zinc is proposed, but the present inventor believes, without wishing to be limited to the theory, that at the root of all the conditions lies a fault in prostaglandin metabolism whereby PG's of the 1-series are lacking or their balance with 2-series PG's is upset. From evidence such as that listed below the inventor believes that zinc increases formation of 1-series PG's selectively, apparently by mediating the mobilisation from ester resources of dihomo-γ-linolenic acid.

Thus zinc is indicated in all the conditions described herein, as favouring 1-series PG synthesis specifically from administered γ-linolenic acid and related materials.

In one group of experiments the test preparation was the isolated superior mesenteric vascular bed, taken from male rats as for example described in the Canadian J. Physiol Pharmacol 54:357, 1976. The perfusion flow rate was at a constant value between 3 to 4 ml/min., pressure 25 to 30 mm Hg, using Krebs bicarbonate buffer containing in mM 150 Na, 4.3 K, 1.0 Mg, 2.5 Ca, 1.7 phosphate, 25 bicarbonate and 11.1 glucose.

Prior to testing the basic vasoconstrictive effect of norepinephrine, as the bitartrate, in successive 10 ng amounts was established, as the amplitude of a transient rise of about 1 min in the perfusion pressure.

Zinc, as the chloride, was then added to the perfusion buffer at successive concentrations and the norepinephrine response measured after 15 minutes at each.

The following results were obtained

| Zinc concentration ($\mu$g/ml) | Response as % of basic level |
| --- | --- |
| 0.1 | 112 |
| 0.2 | 118 |
| 0.4 | 130 |
| 0.8 | 138 |

In the presence of 50 $\mu$g/ml of indomethacin, a known blocking agent for PG synthesis, used with 10 ng/ml PGE 2 to give apparently normal vascular reactivity, the zinc had no effect on the norepinephrine response.

Similar tests with dihomo-γ-linolenic acid and PGE 1 gave respective rises up to a maximum of 130% of the basic response at 50 ng/ml of the acid and a maximum of 150% of the basic response at $2.8 \times 10^{-11}$ M PG.

The results show that zinc gives responses like those of dihomo-γ-linolenic acid and of PGE 1, responses moreover which are not given when PG synthesis is blocked and PGE 2 supplied, and thus that conditions treated with γ-linolenic acid (and thus effectively with dihomo-γ-linolenic acid) may be enhanced in the direction of 1-series PG synthesis by the addition of zinc.

USE OF ANTIBIOTICS

On tests carried out as above, both penicillin V and penicillin G have given responses similar in kind and degree to those given for zinc, supporting further inventor's belief that β-lactam antibiotics are of value in all other conditions treated according to the invention in similar way to the action of zinc and as evidenced in the results with schizophrenia.

I claim:

1. A pharmaceutical or dietary composition for administration to influence the balance of 1-series and 2-series PG's in the body in favor of 1-series PG's, said composition comprising:
   (a) γ-linolenic acid or physiologically functional derivative thereof and/or dihomo-γ-linolenic acid or physiologically functional derivative thereof present in an amount of from about 0.05 to 10 grams calculated as linolenic acid, and
   (b) form about 0.5 to 3 grams of a β-lactam antiobiotic,
   alone or in an acceptable pharmaceutical or dietary vehicle.

2. The composition of claim 1, wherein the antibiotic is a natural or semi-synthetic penicillin or cephalosporin antibiotic.

3. The composition of claim 1, wherein the antibiotic is selected from penicillin G, penicillin N, penicillin V, cephalothin, ampicillin, amoxycillin, cloxacillin, cephalexin and cephaloglycin.

4. The composition of claim 1, presented for administration in doses comprising 0.1 to 5 g of (a) calculated as linolenic acid and 0.5 to 3 g of (b), or one half one third or one quarter of said amounts.

5. The composition of claim 1, presented for administration in doses comprising 0.1 to 2 g of (a) calculated as linolenic acid and 0.5 to 3 g of (b), or one half one third or one quarter of said amounts.

6. The composition of claim 1, presented for administration in doses comprising 0.1 to 1 g of (a) calculated as linolenic acid and 0.5 to 3 g of (b), or one half one third or one quarter of said amounts.

7. A pharmaceutical or dietary composition for administration to influence the balance of 1-series and 2-series PG's in the body in favor of 1-series PG's, said composition comprising:
   (a) γ-linolenic acid or physiologically functional derivative thereof and/or dihomo-γ-linolenic acid or physiologically functional derivative thereof, said acid and/or derivative present in an amount of from about 0.05 to 10 grams calculated as linolenic acid,
   (b) a conjoint amount of about 2.5 to 800 mg of physiologically assimilable zinc calculated as the metal, and
   (c) a β-lactam antibiotic,
   alone or in an acceptable pharmaceutical or dietary vehicle.

8. The composition of claim 7, wherein the antibiotic is a natural or semi-synthetic penicillin or cephalosporin antibiotic.

9. The composition of claim 7, wherein the antibiotic is selected from penicillin G, penicillin N, penicillin V, cephalothin, ampicillin, amoxycillin, cloxacillin, cephalexin and cephaloglycin.

10. The composition of claim 4, presented for administration in doses further comprising (c) 10 to 200 mg assimilable zinc calculated as the metal, or one half one third or one quarter thereof.

11. The composition of claim 5, presented for administration in doses further comprising (c) 10 to 200 mg assimilable zinc calculated as the metal, or one half one third or one quarter thereof.

12. The composition of claim 6, presented for administration in doses further comprising (c) 10 to 200 mg assimilable zinc calculated as the metal, or one half one third or one quarter thereof.

13. The composition of claim 10, 11 or 12, wherein the amount of (c) is 10 to 80 mg calculated as the metal, or one half one third or one quarter thereof.

14. A method of treating schizophrenia comprising administering to a person suffering therefrom an effective amount of a pharmaceutical or dietary composition containing (a) $\gamma$-linolenic acid or physiologically functional derivative thereof and/or dihomo-$\gamma$-linolenic acid or physiologically functional derivative thereof, and (b) a conjoint amount of a further material influencing the 1-series/2-series PG balance in the body in favor of 1-series PGs, said composition being administered alone or in an acceptable pharmaceutical or dietary vehicle.

* * * * *